April 5, 1955 R. G. JELLY Plant Pat. 1,375
ROSE PLANT
Filed Aug. 6, 1954
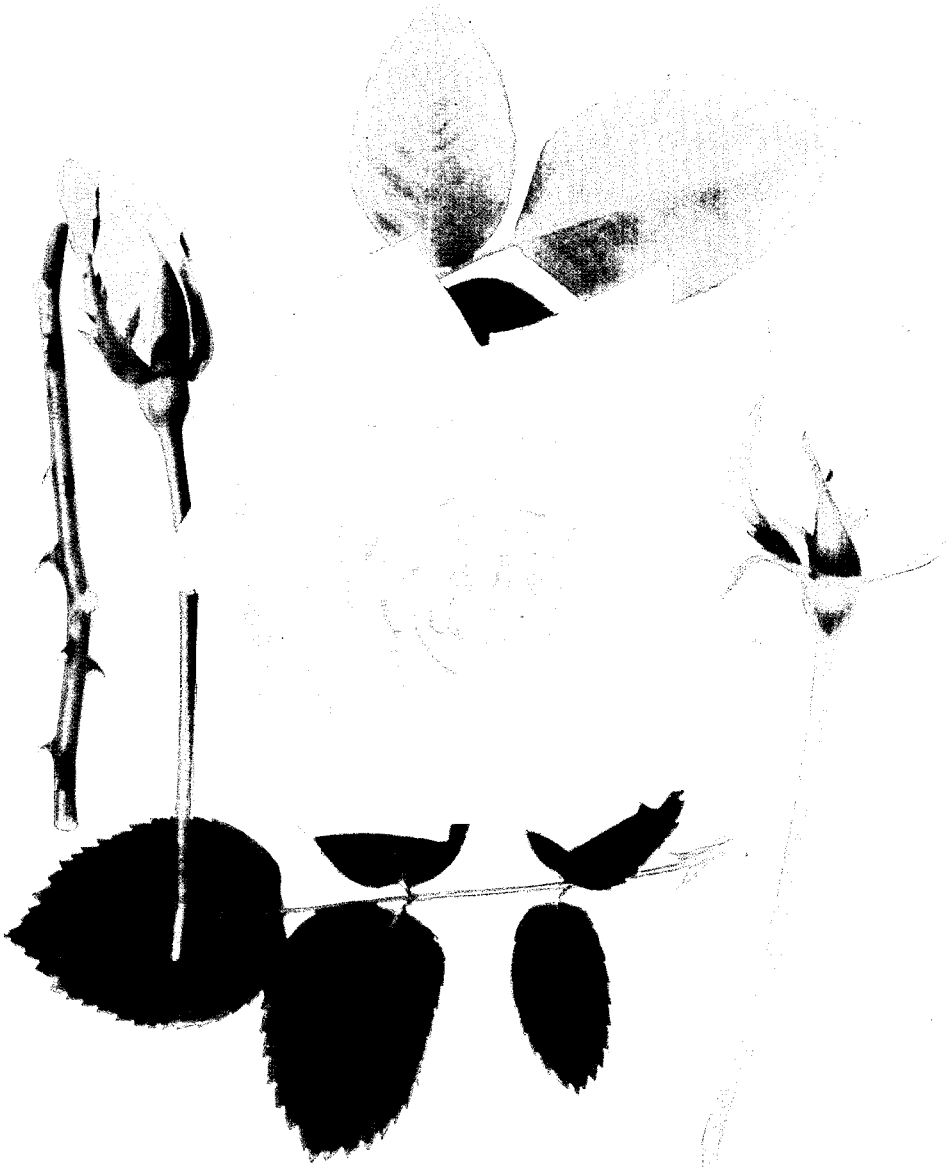
Inventor
R. G. Jelly
By: Robert Robb
attorneys.

United States Patent Office

Plant Pat. 1,375
Patented Apr. 5, 1955

1,375

ROSE PLANT

Robert G. Jelly, Richmond, Ind., assignor to E. G. Hill Co., Inc., Richmond, Ind., a corporation of Indiana Application August 6, 1954, Serial No. 448,403

1 Claim. (Cl. 47—61)

The present invention relates to a new and distinct variety of rose plant of the hybrid tea class, which was originated by me by crossing an unnamed and unpatented seedling with the variety "Pink Bountiful" (Plant Patent No. 601).

The primary objective in making this cross was to improve the flower substance, color and keeping qualities that are so desired by the rose-loving public, while at the same time, combining these characteristics with vigorous and much-branched plant growth habits that are desirable and essential to profitable commercial cut flower production. This objective was fully achieved, as evidenced by the fact that my new variety is endowed with the excellent vigor of both parents, and in addition, is characterized by a superior keeping quality and flower texture, longer stems, upright growth, and a more intense and attractive pink color of the flowers. The buds of the new variety are much larger than those of the pollen parent "Pink Bountiful," said former buds being long-pointed, and the flower stems are much longer and more well-suited to commercial cut flower production.

Generally speaking, the color and growth characteristics of my new variety are somewhat similar to those of the variety "Hope" (patent pending), but is definitely distinguished from the latter by a more desirable size, form and color of the buds, as well as by longer flower stems.

Asexual reproduction of my new variety by grafting at Richmond, Indiana, as well as by budding at San Leandro, California, shows that the foregoing characteristics and distinctions come true to form and are established and transmitted through succeeding propagations.

The accompanying drawing shows typical specimens of the foliage, stems and flowers of my new variety, the latter being shown in different stages of development, as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson"), Koster's Color Guide (hereinafter abbreviated as "Koster") and Ridgway's Color Standards and Nomenclature (hereinafter abbreviated as "Ridgway"), as indicated:

Type: Bush; greenhouse; seedling; for cut flowers.
Class: Hybrid tea.
Breeding: Seedling.
*Seed parent.*—An unnamed seedling.
*Pollen parent.*—"Pink Bountiful."
Propagation: Holds its distinguishing characteristics through succeeding propagations by both grafting and budding.

FLOWER

Locality where grown and observed: Richmond, Indiana.
Flowers borne: 1 to stem; on long, very strong stems.
Quantity of bloom: Free, in greenhouse.
Continuity: Continuous, in greenhouse.
Fragrance: Moderate; sweet.
Bud:
*Peduncle.*—Long; large; very strong; erect; slightly rough; no thorns or hairs, but having numerous prickles colored Chrome Yellow, Plate 605/3 (Wilson). Color—Fern Green, Plate o862 (Wilson).

*Before calyx breaks.* — Size — Medium large. Form—Short-pointed; with conspicuous neck; with foliaceous appendages on the surface of the bud; with slender, much-cut foliaceous parts extending beyond the tip of the bud equal to ¼ of its length. Color—Fern Green, Plate o862 (Wilson).
*As calyx breaks.*—Color—Cardinal Red, Plate 822 (Wilson).
*As first petal opens.*—Size—Large. Form—Long-pointed. Color: Outside—Rose Madder, Plate 23/2 (Wilson); inside—Spinel Pink, Plate o625/2 (Wilson).
*Opening.*—Opens well in greenhouse; normal reduction in bud size results from periods of prolonged hot weather.
Bloom:
*Size (when fully open).*—Large; from 5 inches to 6 inches.
*Petalage.*—Double; from 32 to 48 petals; arranged regularly.
*Form.*—Full and high-centered at first, but becoming open, high-centered; petals being at first tightly rolled outward, but becoming loosely rolled outward later at maturity.
Petals: Moderately thick; leathery; with both inside and outside satiny.
*Shape.*—Outside—Obovate, with apex flat. Intermediate—Obovate, with apex flat. Inside—Obovate, with apex flat.

This description of a newly opened flower was made from a rose grown in a greenhouse in the month of March, at Richmond, Indiana:

Color:
*Outside petal.*—Outside surface—Neyron Rose, Plate 623/1 (Wilson). Inside surface—Rose Pink, Plate 427/1 (Wilson).
*Intermediate petal.*—Outside surface—Tyrian Rose, Plate 24/2 (Wilson). Inside surface—Neyron Rose, Plate 623/2 (Wilson).
*Inner petal.*—Outside surface—Neyron Rose, Plate 623/3 (Wilson). Inside surface—Neyron Rose, Plate 623/2 (Wilson).

This description was made from a rose that was open for 3 days in a greenhouse in the month of March, at Richmond, Indiana:

Color:
*Outside petal.*—Outside surface—Rose Bengal, Plate 25/2 (Wilson). Inside surface—Tyrian Rose, Plate 24/3 (wilson).
*Intermediate petal.*—Outside surface—Rose Bengal, Plate 25/2 (Wilson). Inside surface—Phlox Pink, Plate 625/2 (Wilson).
*Inner petal.*—Outside surface—Rose Bengal, Plate 25/2 (wilson). Inside surface—Phlox Pink, Plate 625/2 (Wilson).
General color effect:
*Newly opened flower.*—Thulite Pink, Plate XXVI (Ridgway).
*3-days open.*—Neyron Rose, Plate 623/2 (Wilson).
Behavior in greenhouse: Persist.
Flower longevity: Cut roses grown in greenhouse and kept at living-room temperatures—6 days in April.

PLANT

Foliage:
*Leaves.*—Compound of 5 leaflets; normally abundant; medium size; moderately leathery.
*Leaflets.*—Shape—Oval, with apex acute. Base—Acute. Margin—Simply serrate.
*Color.*—Mature: Upper surface—Ivy Green, Plate ooo1060/2 (Wilson); under surface—Sage Green, Plate ooo861/1 (Wilson). Young: Upper surface—Spinach Green, Plate o60/1 (Wilson); under surface — Asphodel Green, Plate XLI (Ridgway).
*Rachis (the supporting stem of the compound leaf).*—Medium. Upper side—Prickly. Under side—Moderately thorny.

*Stipules.*—Medium length; medium width; with medium length points which turn out at an angle of more than 45°; recurved toward stem.

Growth:

*Habit.*—Upright; much-branched.

*Growth.*—Free; vigorous.

*Canes.*—Medium diameter.

*Main stems.*—Color—Parsley Green, Plate oo962 (Wilson). Thorns—Several; medium length; hooked downward; with narrow base. Color—Yellow Ochre, Plate o7 (Wilson). Prickles—None. Hairs—None.

*Branches.*—Color—Spinach Green, Plate o960/2 (Wilson). Thorns—Several; medium length; hooked downward; with narrow base. Color—Chrysanthemum Crimson, Plate 824 (Wilson). Prickles—None. Hairs—None.

*New shoots.*—Color—Scheele's Green, Plate 860 (Wilson). Thorns—Several; medium length; hooked downward; with short, narrow base. Color—French Purple, Plate 42 (Koster). Prickles—Present only near tip of shoot. Color—Cream Yellow, Plate 4 (Koster). Hairs—None.

REPRODUCTIVE ORGANS

Stamens: Many; arranged regularly about pistils; mixed with petaloids and tucked in calyx.

Filaments: Medium length; most with anthers.

*Color.*—Nasturtium Orange, Plate 610/1 (Wilson).

Anthers: Medium; all open at once.

*Color.*—Yellow Ochre, Plate o7 (Wilson).

Pollen: Moderate.

*Color.*—Indian Yellow, Plate 6/1 (Wilson).

Pistils: Medium number.

Styles: Even; medium length; medium heavy; bunched; columnar.

*Color.*—Cherry, Plate 722 (Wilson).

Stigma:

*Color.*—Nasturtium Orange, Plate 610/3 (Wilson).

Ovaries: Some protruding from calyx.

Hips: Medium length; flat; with conspicuous neck; tulip-shaped; moderately rough; walls thick.

*Color.*—Orange, Plate 12 (Koster); a great portion of the orange color is masked by overlain brown similar in appearance to alligator skin.

Sepals: Permanent; medium length; spear-shaped; recurved slightly.

*Color.*—Inside—Willow Green, Plate ooo862/1 (Wilson). Outside—Spinach Green, Plate o960 (Wilson).

Seeds: Medium number; medium size.

I claim:

A new and distinct variety of rose plant of the hybrid tea class, substantially as herein shown and described, characterized particularly as to novelty by its superior vigor, upright and much-branched habits of growth, the superior keeping quality and texture of its flowers, its relatively long flower stems, its long-pointed and relatively large buds, and the distinctive and intense pink general color tonality of its buds and flowers.

No references cited.